US007148230B2

(12) United States Patent
Bradbury et al.

(10) Patent No.: US 7,148,230 B2
(45) Date of Patent: Dec. 12, 2006

(54) QUINAZOLINE DERIVATIVES

(75) Inventors: Robert Hugh Bradbury, Macklesfield (GB); Jason Grant Kettle, Macklesfield (GB); James McCabe, Macklesfield (GB); Andrew Turner, Macklesfield (GB); Laurent Francois Andre Hennequin, Reims (FR)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 10/857,342

(22) Filed: Jun. 1, 2004

(65) Prior Publication Data

US 2005/0165035 A1 Jul. 28, 2005

(30) Foreign Application Priority Data

Jul. 29, 2003 (GB) .................. 0317665.8

(51) Int. Cl.
*A61K 31/517* (2006.01)
*C07D 43/02* (2006.01)
(52) U.S. Cl. .............. 514/266.22; 514/266.4; 544/284; 544/293
(58) Field of Classification Search .......... 514/266.22, 514/266.4; 544/284, 293
See application file for complete search history.

(56) References Cited

U.S. PATENT DOCUMENTS

| 3,985,749 | A | 10/1976 | Foster | |
| 5,252,586 | A | 10/1993 | Cain et al. | 514/317 |
| 5,457,105 | A | 10/1995 | Barker | 514/234.5 |
| 5,616,582 | A | 4/1997 | Barker | 514/234.5 |
| 5,747,498 | A | 5/1998 | Schnur et al. | 514/266.4 |
| 5,770,599 | A | 6/1998 | Gibson | 514/228.2 |
| 5,770,603 | A | 6/1998 | Gibson | 514/266.24 |
| 5,821,246 | A | 10/1998 | Brown et al. | 514/252.17 |
| 5,866,572 | A | 2/1999 | Barker et al. | 514/234.5 |
| 6,004,967 | A | 12/1999 | McMahon et al. | 514/266.4 |
| 6,126,917 | A * | 10/2000 | Mishani et al. | 424/1.89 |
| 6,177,433 | B1 * | 1/2001 | Uckun et al. | 514/266.4 |
| 6,225,318 | B1 * | 5/2001 | Sobolov-Jaynes et al. | 514/266.2 |
| 6,653,305 | B1 * | 11/2003 | Himmelsbach et al. | 514/233.5 |
| 6,740,651 | B1 * | 5/2004 | Himmelsbach et al. | 514/228.8 |
| 6,924,285 | B1 * | 8/2005 | Himmelsbach et al. | 514/234.8 |
| 2002/0049197 | A1 * | 4/2002 | Himmelsbach et al. | 514/217.06 |
| 2002/0082271 | A1 * | 6/2002 | Himmelsbach et al. | 514/266.24 |
| 2002/0169180 | A1 * | 11/2002 | Himmelsbach et al. | 514/266.4 |
| 2002/0173509 | A1 * | 11/2002 | Himmelsbach et al. | 514/234.5 |
| 2002/0177601 | A1 * | 11/2002 | Himmelsbach et al. | 514/266.2 |
| 2003/0149062 | A1 * | 8/2003 | Jung et al. | 514/266.22 |
| 2003/0158196 | A1 * | 8/2003 | Jung et al. | 514/234.2 |
| 2004/0044014 | A1 * | 3/2004 | Himmelsbach et al. | 514/266.4 |
| 2004/0048880 | A1 * | 3/2004 | Himmelsbach et al. | 514/266.2 |
| 2005/0215574 | A1 | 9/2005 | Bradbury et al. | |

FOREIGN PATENT DOCUMENTS

| EP | 0520722 B1 | 12/1992 |
| EP | 0566226 B1 | 10/1993 |
| EP | 0602851 B1 | 6/1994 |
| EP | 0 607 439 | 7/1994 |
| EP | 0635507 B1 | 1/1995 |
| EP | 1283039 A1 | 2/2003 |
| GB | 2033894 | 5/1980 |
| GB | 2160201 | 12/1985 |
| WO | WO 92/14746 | 9/1992 |
| WO | 92/20642 | 11/1992 |
| WO | 94/27965 | 12/1994 |
| WO | WO 95/00146 | 1/1995 |
| WO | WO 95/03283 | 2/1995 |
| WO | 95/15758 | 6/1995 |
| WO | 95/24190 | 9/1995 |
| WO | 96/15118 | 5/1996 |
| WO | 96/33981 | 9/1996 |
| WO | 96/30347 | 10/1996 |
| WO | 96/33977 | 10/1996 |
| WO | 96/33978 | 10/1996 |
| WO | 96/33979 | 10/1996 |
| WO | 96/33980 | 10/1996 |
| WO | 97/03069 | 1/1997 |
| WO | 97/18813 | 5/1997 |
| WO | 97/22596 | 6/1997 |

(Continued)

OTHER PUBLICATIONS

March J., Advanced Organic Chemistry—Reactions, Mechanisms, and Structure, 4$^{th}$ Ed., © 1992, John Wiley & Sons, New York, NY, p. 357.*

(Continued)

*Primary Examiner*—James O. Wilson
*Assistant Examiner*—Tamthom N. Truong
(74) *Attorney, Agent, or Firm*—Finnegan, Henderson, Farabow, Garrett & Dunner, LLP.

(57) ABSTRACT

The invention concerns quinazoline derivatives of Formula I

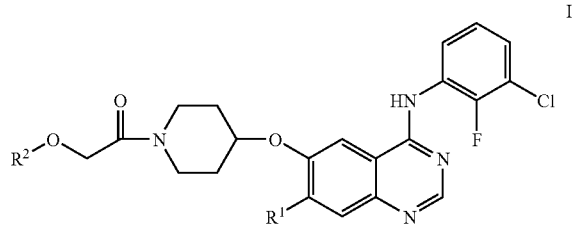

wherein $R^1$ and $R^2$ have any of the meanings defined in the description; processes for their preparation, pharmaceutical compositions containing them and their use in the manufacture of a medicament for use as an antiproliferative agent in the prevention or treatment of tumours which are sensitive to inhibition of erbB, particularly EGF, receptor tyrosine kinases.

5 Claims, No Drawings

FOREIGN PATENT DOCUMENTS

| | | |
|---|---|---|
| WO | 97/30034 | 8/1997 |
| WO | 97/30035 | 8/1997 |
| WO | 97/32856 | 9/1997 |
| WO | 97/38994 | 10/1997 |
| WO | 97/42187 | 11/1997 |
| WO | 98/13354 | 4/1998 |
| WO | 98/389884 | 9/1998 |
| WO | 99/10349 | 3/1999 |
| WO | 00/10981 | 3/2000 |
| WO | 00/12497 | 3/2000 |
| WO | 00/20402 | 4/2000 |
| WO | 00/51991 | 8/2000 |
| WO | 00/51587 | 9/2000 |
| WO | 00/55141 | 9/2000 |
| WO | 00/55162 | 9/2000 |
| WO | 00/56338 | 9/2000 |
| WO | 00/56720 | 9/2000 |
| WO | 00/68203 | 11/2000 |
| WO | 00/78735 A1 | 12/2000 |
| WO | 01/04102 A1 | 1/2001 |
| WO | 01/21594 A1 | 3/2001 |
| WO | 01/21595 A1 | 3/2001 |
| WO | 01/21596 A1 | 3/2001 |
| WO | 01/32651 A1 | 5/2001 |
| WO | 01/66099 A2 | 9/2001 |
| WO | 01/66099 A3 | 9/2001 |
| WO | 01/76586 A1 | 10/2001 |
| WO | 01/77085 A1 | 10/2001 |
| WO | 01/94341 A1 | 12/2001 |
| WO | 02/16352 A1 | 2/2002 |
| WO | 02/18351 A1 | 3/2002 |
| WO | 02/18370 A1 | 3/2002 |
| WO | 02/18372 A1 | 3/2002 |
| WO | 02/18373 A1 | 3/2002 |
| WO | 02/18376 A1 | 3/2002 |
| WO | 02/34711 A1 | 5/2002 |
| WO | 02/41882 A2 | 5/2002 |
| WO | 02/41882 A3 | 5/2002 |
| WO | 02/50043 A1 | 6/2002 |
| WO | 02/092577 A1 | 11/2002 |
| WO | 02/092578 A1 | 11/2002 |
| WO | WO 02/092579 | 11/2002 |
| WO | 03/000188 A2 | 1/2003 |
| WO | 03/000188 A3 | 1/2003 |
| WO | 03/040108 A1 | 5/2003 |
| WO | 03/040109 A2 | 5/2003 |
| WO | 03/040109 A3 | 5/2003 |
| WO | 03/045364 A2 | 6/2003 |
| WO | 03/045364 A3 | 6/2003 |
| WO | 03/045395 A1 | 6/2003 |
| WO | 03/082290 A1 | 10/2003 |
| WO | 03/082831 A1 | 10/2003 |
| WO | WO 2005/028469 | 3/2005 |
| WO | WO 2005/028470 | 3/2005 |
| WO | WO 2005/030757 | 4/2005 |

OTHER PUBLICATIONS

Bridges et al., J. Med. Chem., 1996, 39(1), 267-276.
Chevalier et al., J. Cell Science, 1999, 112(24), 4785-4791.
Gazit et al., Bioorg. Med. Chem., 1996, 4(8), 1203-1207.
Ghosh et al., Anti-Cancer Drug Des., 1999, 14(5), 403-410.
Hennequin et al., J. Med. Chem., 1999, 42(26), 5369-5389.
Hennequin et al., J. Med. Chem., 2002, 45, 1300-1312.
Myers et al., Bioorg. Med. Chem. Lett., 1997, 7(4), 417-420.
Rewcastle, J. Med. Chem., 1995, 38, 3482-3487.
Singh et al., J. Enzyme Inhibition, 1998, 13(2) 125-134.
Small et al., J. Med. Chem., 2000, 43(16), 3199.
Wright et al., Biorg. Med. Chem. Lett., 2001, 11(1), 17-21.
"Status of Epidermal Growth Factor Receptor Antagonists in the Biology and Treatment of Cancer" by Mendelsohn et al., Journal of Clinical Oncology, vol. 21, No. 14 (Jul. 2003), pp. 2787-2799.
"Targeting the Epidermal Growth Factor Receptor for Cancer Therapy" by Mendelsohn, Journal of Clinical Oncology, vol. 20, No. 18s (Sep. 15 Supplement) 2002, pp. 2s-13s.
"Epidermal Growth Factor Receptor Mutations, Small-Molecule Inhibitors, and Non-Small-Cell Lung Cancer: Current Knowledge and Future Directions" by Pao et al., Journal of Clinical Oncology, vol. 23, No. 11, Apr. 10, 2005.

* cited by examiner

QUINAZOLINE DERIVATIVES

The invention concerns certain novel quinazoline derivatives, or pharmaceutically-acceptable salts, or a pharmaceutically acceptable ester thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Many of the current treatment regimes for diseases resulting from the abnormal regulation of cellular proliferation such as psoriasis and cancer, utilise compounds that inhibit DNA synthesis and cellular proliferation. To date, compounds used in such treatments are generally toxic to cells however their enhanced effects on rapidly dividing cells such as tumour cells can be beneficial. Alternative approaches to these cytotoxic anti-tumour agents are currently being developed, for example selective inhibitors of cell signalling pathways. These types of inhibitors are likely to have the potential to display an enhanced selectivity of action against tumour cells and so are likely to reduce the probability of the therapy possessing unwanted side effects.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al, *Curr Opin Chem Biol*, 1999, 3, 459–465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al, *Biochimica et Biophysica Acta*, 1997, 133, F217–F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases e.g. EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised in to 20 receptor tyrosine kinase and 10 non-receptor tyrosine kinase sub-families (Robinson et al, *Oncogene*, 2000, 19, 5548–5557).

The receptor tyrosine kinases are of particular importance in the transmission of mitogenic signals that initiate cellular replication. These large glycoproteins, which span the plasma membrane of the cell possess an extracellular binding domain for their specific ligands (such as Epidermal Growth Factor (EGF) for the EGF Receptor). Binding of ligand results in the activation of the receptor's kinase enzymatic activity that is encoded by the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.*, 2000, 19, 3159). One mechanism in which this can be accomplished is by overexpression of the receptor at the protein level, generally as a result of gene amplification. This has been observed in many common human cancers (reviewed in Klapper et al., *Adv. Cancer Res.*, 2000, 77, 25) such as breast cancer (Sainsbury et al., *Brit. J. Cancer*, 1988, 58, 458; Guerin et al., *Oncogene Res.*, 1988, 3, 21; Slamon et al., *Science*, 1989, 244, 707; Klijn et al., *Breast Cancer Res. Treat.*, 1994, 29, 73 and reviewed in Salomon et al., *Crit. Rev. Oncol. Hematol.*, 1995, 19, 183), non-small cell lung cancers (NSCLCs) including adenocarcinomas (Cerny et al., *Brit. J. Cancer*, 1986, 54, 265; Reubi et al., *Int. J. Cancer*, 1990, 45, 269; Rusch et al., *Cancer Research*, 1993, 53, 2379; Brabender et al, *Clin. Cancer Res.*, 2001, 7, 1850) as well as other cancers of the lung (Hendler et al., *Cancer Cells*, 1989, 7, 347; Ohsaki et al., *Oncol. Rep.*, 2000, 7, 603), bladder cancer (Neal et al., *Lancet*, 1985, 366; Chow et al., *Clin. Cancer Res.*, 2001, 7, 1957, Zhau et al., *Mol Carcinog.*, 3, 254), oesophageal cancer (Mukaida et al., *Cancer*, 1991, 68, 142), gastrointestinal cancer such as colon, rectal or stomach cancer (Bolen et al., *Oncogene Res.*, 1987, 1, 149; Kapitanovic et al., *Gastroenterology*, 2000, 112, 1103; Ross et al., *Cancer Invest.*, 2001, 19, 554), cancer of the prostate (Visakorpi et al., *Histochem. J.*, 1992, 24, 481; Kumar et al., 2000, 32, 73; Scher et al., *J. Natl. Cancer Inst.*, 2000, 92, 1866), leukaemia (Konaka et al., *Cell*, 1984, 37, 1035, Martin-Subero et al., *Cancer Genet Cytogenet.*, 2001, 127, 174), ovarian (Hellstrom et al., *Cancer Res.*, 2001, 61, 2420), head and neck (Shiga et al., *Head Neck*, 2000, 22, 599) or pancreatic cancer (Ovotny et al., *Neoplasma*, 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors, it is widely believed that many tumours become clinically more aggressive and so correlate with a poorer prognosis for the patient (Brabender et al, *Clin. Cancer Res.*, 2001, 7, 1850; Ross et al, *Cancer Investigation*, 2001, 19, 554, Yu et al., *Bioessays*, 2000, 22.7, 673). In addition to these clinical findings, a wealth of pre-clinical information suggests that the erbB family of receptor tyrosine kinases are involved in cellular transformation. This includes the observations that many tumour cell lines over-express one or more of the erbB receptors and that EGFR or erbB2 when transfected into non-tumour cells have the ability to transform these cells. This tumourigenic potential has been further verified as transgenic mice that overexpress erbB2 spontaneously develop tumours in the mammary gland. In addition to this, a number of pre-clinical studies have demonstrated that anti-proliferative effects can be induced by knocking out one or more erbB activities by small molecule inhibitors, dominant negatives or inhibitory antibodies (reviewed in Mendelsohn et al., *Oncogene*, 2000, 19, 6550). Thus it has been recognised that inhibitors of these receptor tyrosine kinases should be of value as a selective inhibitor of the proliferation of mammalian cancer cells (Yaish et al. *Science*, 1988, 242, 933, Kolibaba et al, Biochimica et Biophysica Acta, 1997, 133, F217–F248; Al-Obeidi et al, 2000, *Oncogene*, 19, 5690–5701; Mendelsohn et al, 2000, *Oncogene*, 19, 6550–6565).

Recently the small molecule EGFR tyrosine kinase inhibitor, Iressa (also known as gefitinib, and ZD1834) has been approved for use in the treatment of advanced non-small cell lung cancer. Furthermore, findings using inhibitory antibodies against EGFR and erbB2 (c-225 and trastuzumab respectively) have proven to be beneficial in the clinic for the treatment of selected solid tumours (reviewed in Mendelsohn et al, 2000, *Oncogene*, 19, 6550–6565).

Amplification and/or activity of members of the erbB receptor tyrosine kinases have been detected and so have been implicated to play a role in a number of non-malignant proliferative disorders such as psoriasis (Ben-Bassat, *Curr. Pharm. Des.*, 2000, 6, 933; Elder et al., Science, 1989, 243, 811), benign prostatic hyperplasia (BPH) (Kumar et al., *Int. Urol. Nephrol.*, 2000, 32, 73), atherosclerosis and restenosis (Bokemeyer et al., *Kidney Int.*, 2000, 58, 549). It is therefore expected that inhibitors of erbB type receptor tyrosine kinases will be useful in the treatment of these and other non-malignant disorders of excessive cellular proliferation.

European patent application EP 566 226 discloses certain 4-anilinoquinazolines that are receptor tyrosine kinase inhibitors.

International patent applications WO 96/33977, WO 96/33978, WO 96/33979, WO 96/33980, WO 96/33981, WO 97/30034, WO 97/38994 disclose that certain quinazoline derivatives which bear an anilino substituent at the 4-position and a substituent at the 6- and/or 7-position possess receptor tyrosine kinase inhibitory activity.

European patent application EP 837 063 discloses aryl substituted 4-aminoquinazoline derivatives carrying moiety containing an aryl or heteroaryl group at the 6- or 7-position on the quinazoline ring. The compounds are stated to be useful for treating hyperproliferative disorders.

International patent applications WO 97/30035 and WO 98/13354 disclose certain 4-anilinoquinazolines substituted at the 7-position are vascular endothelial growth factor receptor tyrosine kinase inhibitors.

WO 00/55141 discloses 6,7-substituted 4-anilinoquinazoline compounds characterised in that the substituents at the 6- and/or 7-position carry an ester linked moiety (RO—CO).

WO 00/56720 discloses 6,7-dialkoxy-4-anilinoquinazoline compounds for the treatment of cancer or allergic reactions.

WO 02/41882 discloses 4-anilinoquinazoline compounds substituted at the 6- and/or 7-position by a substituted pyrrolidinyl-alkoxy or piperidinyl-alkoxy group.

Co-pending PCT application number PCT/GB03/01306 (published after the priority date of the present application as WO 03/082831) discloses 4-(2,3-dihalogenoanilino) quinazoline compounds substituted at the 6-position by a heterocyclyloxy or heterocyclylalkoxy group which are erbB, particularly EGFR tyrosine kinase inhibitors. PCT application number PCT/GB03/01306 discloses as example 16 the compound 6-(1-Acetylpiperidin-4-yloxy)-4-(3-chloro-2-fluoroanilino)-7-methoxyquinazoline:

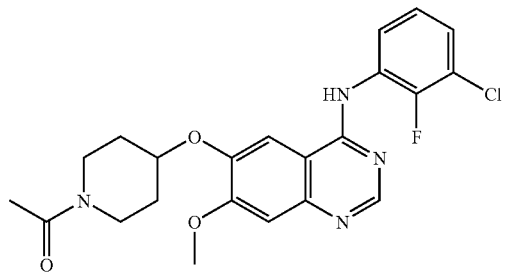

and as Example 28 the compound 4-(3-Chloro-2-fluoroanilino)-6-[1-(hydroxyacetyl)piperidin-3-yloxy]-7-methoxyquinazoline:

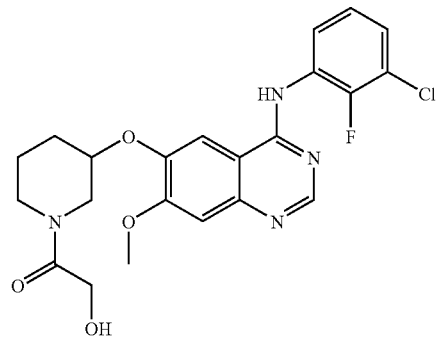

We have now surprisingly found that certain 4-(3-Chloro-2-fluoroanilino)quinazoline compounds substituted at the 6-position by a substituted piperidin-4-yl group possess potent in-vivo anti-tumour activity and have a number of other favourable properties including improved cell and in-vivo potency and/or advantageous DMPK properties, for example high bioavailability and/or high free-plasma levels and/or advantageous half life and/or advantageous volume of distribution and/or good physical properties such as solubility. Furthermore, the compounds according to the present invention are expected to be inactive or only weakly active in a hERG assay.

Without wishing to imply that the compounds disclosed in the present invention possess pharmacological activity only by virtue of an effect on a single biological process, it is believed that the compounds provide an anti-tumour effect by way of inhibition of one or more of the erbB family of receptor tyrosine kinases that are involved in the signal transduction steps which lead to the proliferation of tumour cells. In particular, it is believed that the compounds of the present invention provide an anti-tumour effect by way of inhibition of EGFR tyrosine kinase.

Generally the compounds of the present invention possess potent inhibitory activity against the erbB receptor tyrosine kinase family, for example by inhibition of EGFR and/or erbB2 and/or erbB4 receptor tyrosine kinases, whilst possessing less potent inhibitory activity against other kinases. Furthermore, the compounds of the present invention possess substantially better potency against the EGFR tyrosine kinase over that of the erbB2 tyrosine kinase. Accordingly, it may be possible to administer a compound according to the present invention at a dose that is sufficient to inhibit EGFR tyrosine kinase whilst having no significant effect upon erbB2 (or other) tyrosine kinases. The selective inhibition provided by the compounds according to the present invention may provide treatments for conditions mediated by EGFR tyrosine kinase, whilst, for example, reducing undesirable side effects that may be associated with the inhibition of other tyrosine kinases.

According to a first aspect of the invention there is provided a quinazoline derivative of the Formula I:

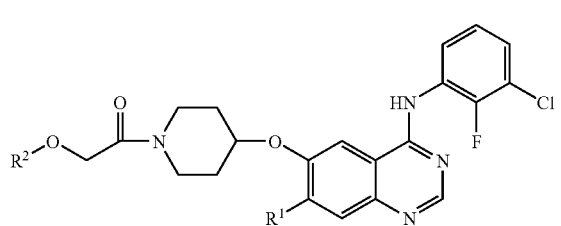

wherein:
$R^1$ is selected from hydrogen and methoxy; and
$R^2$ is hydrogen;

or a pharmaceutically acceptable salt, or a pharmaceutically acceptable ester thereof.

It is to be understood that certain compounds of the Formula I may exist in solvated as well as unsolvated forms such as, for example, hydrated forms. It is to be understood that the invention encompasses all such solvated forms which possess antiproliferative activity.

It is also to be understood that certain compounds of the Formula I may exhibit polymorphism, and that the invention encompasses all such forms which possess antiproliferative activity.

A suitable pharmaceutically acceptable salt of a compound of the Formula I is, for example, an acid-addition salt of a compound of the Formula I, for example an acid-addition salt with an inorganic or organic acid. Suitable inorganic acids include, for example, hydrochloric, hydrobromic or sulfuric acid. Suitable organic acids include, for example, trifluoroacetic, citric, maleic, tartaric, fumaric, methanesulfonic or 4-toluenesulfonic acid. In one embodiment of the invention a particular pharmaceutically acceptable acid addition salt is, for example, a salt formed with an organic acid such as maleic, tartaric or methanesulfonic acid. We have found that these salts possess advantageous properties for example compared to the free base form of the quinazoline derivative of the Formula I, for example improved dissolution rate and/or pharmacodynamic properties such as improved bioavailability.

Generally it is preferable that the pharmaceutically acceptable salts of the quinazoline derivatives of the Formula I are crystalline, because amongst other things, this enables the quinazoline derivative to be prepared in high purity. When it is stated herein that a quinazoline derivative of the Formula I is crystalline, the degree of crystallinity as determined by X-ray powder diffraction data is conveniently greater than about 60%, more conveniently greater than about 70%, preferably greater than about 80% and more preferably greater than about 90%, still more preferably greater than about 95%. Most preferably, the degree of crystallinity as determined by X-ray powder diffraction data is greater than about 98%. The determination of the degree of crystallinity using X-ray powder diffraction is well known to those skilled in the art.

The term "pharmaceutically acceptable ester" used herein refers to an ester of a quinazoline derivative of the Formula I which hydrolyses in vivo to leave the parent compound or a pharmaceutically acceptable salt thereof. An in-vivo hydrolysable ester of a quinazoline of Formula I may be used to alter or improve the physical and/or pharmacokinetic profile of the parent compound, for example the solubility. Suitable ester groups that may be used in the formation of pharmaceutically acceptable ester prodrugs are well known, for example as discussed in for example:

Pro-drugs as Novel Delivery Systems, T. Higuchi and V. Stella, Vol. 14 of the ACS Symposium Series, and in Edward B. Roche, ed.;

Bioreversible Carriers in Drug Design, American Pharmaceutical Association and Pergamon Press, 1987;

Design of Prodrugs, edited by H. Bundgaard, (Elsevier, 1985) and Methods in Enzymology, Vol. 42, p. 309–396, edited by K. Widder, et al. (Academic Press, 1985);

A Textbook of Drug Design and Development, edited by Krogsgaard-Larsen and H. Bundgaard, Chapter 5 "Design and Application of Prodrugs", by H. Bundgaard p. 113–191 (1991);

H. Bundgaard, Advanced Drug Delivery Reviews, 8, 1–38 (1992);

H. Bundgaard, et al., Journal of Pharmaceutical Sciences, 77, 285 (1988); and

N. Kakeya, et al., Chem Pharm Bull, 32, 692 (1984).

A particular pharmaceutically acceptable ester of a quinazoline derivative of the Formula I or a pharmaceutically-acceptable salt thereof is, an ester formed with the hydroxy group represented by $OR^2$ in Formula I, which ester is hydrolysed in the human or animal body to produce the parent quinazoline of Formula I when administered to a warm blooded animal such as a human. Examples of such pharmaceutically acceptable esters of a quinazoline derivative of the Formula I or a pharmaceutically-acceptable salt thereof include inorganic esters such as phosphate esters, α-acyloxyalkyl ethers and related compounds, and esters derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Following administration, the pharmaceutically acceptable ester undergoes in-vivo hydrolysis breakdown to give the parent hydroxy group in the quinazoline derivative of Formula I. Examples of α-acyloxyalkyl ethers include acetoxymethoxy and 2,2-dimethylpropionyloxymethoxy. A selection of pharmaceutically acceptable ester forming groups for the hydroxy group in Formula I include (1–6C)alkanoyl, benzoyl, phenylacetyl and substituted benzoyl and phenylacetyl, (1–6C)alkoxycarbonyl (to give alkyl carbonate esters), di-(1–4C)alkylcarbamoyl and N-(di-(1–4C)alkylaminoethyl)-N-(1–4C)alkylcarbamoyl (to give carbamates), di-(1–4C)alkylaminoacetyl and carboxyacetyl. Examples of substituents on benzoyl include chloromethyl or aminomethyl, (1–4C)alkylaminomethyl and di-((1–4C)alkyl)aminomethyl, and morpholino or piperazino linked from a ring nitrogen atom via a methylene linking group to the 3- or 4-position of the benzoyl ring.

Particular pharmaceutically acceptable esters are phosphate esters formed with the hydroxy group in the quinazoline derivative for the Formula I, or a pharmaceutically acceptable salt thereof. More particularly, pharmaceutically acceptable esters include quinazoline derivatives of the Formula I in which the hydroxy represented by $OR^2$ in Formula I forms a phosphoryl (npd is 1) or phosphiryl (npd is 0) ester of the formula (PD1), or a pharmaceutically acceptable salt thereof:

(PD1)

Another particular pharmaceutically acceptable ester is a quinazoline derivative of the Formula I in which the hydroxy represented by OR² in Formula I forms a phosphoryl to give a group of the formula (PD1) wherein npd is 1.

Useful intermediates for the preparation of such esters include compounds containing a group of formula (PD1) in which either or both of the —OH groups in (PD1) is independently protected by (1–4C)alkyl (such compounds also being interesting compounds in their own right), phenyl or phenyl-(1–4C)alkyl (such phenyl groups being optionally substituted by 1 or 2 groups independently selected from (1–4C)alkyl, nitro, halo and (1–4C)alkoxy).

Pharmaceutically acceptable esters of a quinazoline derivative of Formula I containing a group such as (PD1), may be prepared by reaction of a quinazoline derivative Formula I with a suitably protected phosphorylating agent (for example, containing a chloro or dialkylamino leaving group), followed by oxidation (if necessary) and deprotection. Suitable phosphorylating agents are well known and include, for example protected phosphoramidite compounds such as a N,N-di-[(1–6C)alkyl]-phosphoramidite, for example di-tert-butyl N,N-diethylphosphoramidite.

It is to be understood that an ester group in the quinazoline derivative of the Formula I may form a pharmaceutically acceptable salt of the ester group and that such salts form part of the present invention. Where pharmaceutically acceptable salts of a pharmaceutically acceptable ester is required this is achieved by conventional techniques well known to those of ordinary skill in the art. Thus, for example, compounds containing a group of formula (PD1), may ionise (partially or fully) to form salts with an appropriate number of counter-ions. By way of example, if a pharmaceutically acceptable ester pro-drug of a quinazoline derivative Formula I contains a (PD1) group, there are two HO—P— functionalities present, each of which may form an appropriate salt with a suitable counter-ion. Suitable salts of a group of the formula (PD1) are base salts such as an alkali metal salt for example sodium, an alkaline earth metal salt for example calcium or magnesium or an organic amine salt for example triethylamine, or tris-(2-hydroxyethyl) amine. Thus for example the group (PD1) may form, a mono- or di-sodium salt).

A preferred compound of the invention is a quinazoline derivative of the Formula I which is:
4-(3-chloro-2-fluoroanilino)-6-[1-(hydroxyacetyl)piperidin-4-yloxy]-7-methoxyquinazoline; or a pharmaceutically acceptable salt thereof (preferably a pharmaceutically acceptable acid addition salt), or a pharmaceutically acceptable ester thereof.

In an embodiment of the invention there is provided a quinazoline derivative of the Formula (I) as hereinbefore defined, or a pharmaceutically acceptable salt thereof.

In this specification the generic term "alkyl" includes both straight-chain and branched-chain alkyl groups such as propyl, isopropyl and tert-butyl, and (3–7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only. An analogous convention applies to other generic terms, for example (1–6C)alkoxy includes methoxy, ethoxy, cyclopropyloxy and cyclopentyloxy, (1–6C)alkylamino includes methylamino, ethylamino, cyclobutylamino and cyclohexylamino, and di-[(1–6Calkyl] amino includes dimethylamino, diethylamino, N-cyclobutyl-N-methylamino and N-cyclohexyl-N-ethylamino.

Suitable values for any of various groups defined hereinbefore or hereafter in this specification include:

| | |
|---|---|
| for halogeno | fluoro, chloro, bromo and iodo; |
| for (1-6C)alkyl: | methyl, ethyl, propyl, isopropyl, tert-butyl, pentyl and hexyl; |
| for (1-6C)alkoxy: | methoxy, ethoxy, propoxy, isopropoxy and butoxy; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbonyl, ethoxycarbonyl, propoxycarbonyl and tert-butoxycarbonyl; |
| for N-(1-6C) alkylcarbamoyl: | N-methylcarbamoyl, N-ethylcarbamoyl, N-propylcarbamoyl and N-isopropylcarbamoyl; |
| for N,N-di-[(1-6C)alkyl] carbamoyl: | N,N-dimethylcarbamoyl, N-ethyl-N-methylcarbamoyl and N,N-diethylcarbamoyl; |
| for (2-6C)alkanoyl: | acetyl, propionyl and isobutyryl; and |
| for (2-6C)alkanoyloxy: | acetoxy and propionyloxy. |

Synthesis of Quinazoline Derivatives of the Formula I

A further aspect the present invention provides a process for preparing a quinazoline derivative of Formula I or a pharmaceutically-acceptable salt, or a pharmaceutically acceptable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

The protecting groups may be removed at any convenient stage in the synthesis using conventional techniques well known in the chemical art.

A quinazoline derivative of the Formula I, or a pharmaceutically acceptable salt or a pharmaceutically acceptable ester thereof, may be prepared by any process known to be applicable to the preparation of chemically-related compounds, for example using analogous processes to those described in WO 03/082831. Such processes, when used to prepare a quinazoline derivative of the Formula I, or a pharmaceutically-acceptable salt or a pharmaceutically acceptable ester thereof, are provided as a further feature of the invention and are illustrated by the following representative process variants. Necessary starting materials may be obtained by standard procedures of organic chemistry (see, for example, Advanced Organic Chemistry (Wiley-Interscience), Jerry March). The preparation of such starting materials is described within the accompanying non-limiting Examples. Alternatively, necessary starting materials are obtainable by analogous procedures to those illustrated which are within the ordinary skill of an organic chemist.

In the following process for the preparation of quinazoline derivatives of the Formula I, or pharmaceutically acceptable salts, or pharmaceutically acceptable esters thereof, the variables are as defined above unless stated otherwise.

By coupling, conveniently in the presence of a suitable base, a compound of the Formula II, or a salt thereof:

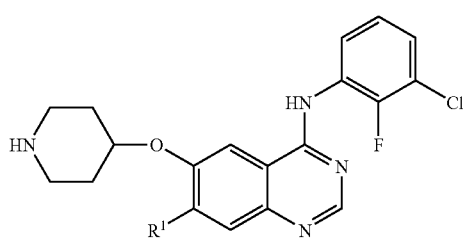

wherein $R^1$ is as hereinbefore defined, and any functional group in the compound of Formula II is protected if necessary, with a carboxylic acid of Formula III, or a reactive derivative thereof:

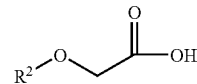

wherein $R^2$ is as hereinbefore defined, and any functional group in the compound of Formula II is protected if necessary;

and thereafter, if necessary (in any order):
(i) removing any protecting groups by conventional techniques;
(ii) forming a pharmaceutically acceptable salt; and
(iii) forming a pharmaceutically acceptable ester.

Specific conditions for the above reactions are as follows:

The coupling reaction is conveniently carried out in the presence of a suitable coupling agent, such as a carbodiimide such as dicyclohexylcarbodiimide, or a suitable peptide coupling agent, for example O-(7-azabenzotriazol-1-yl)-N,N,N',N'-tetramethyluronium hexafluoro-phosphate (HATU). The coupling reaction is conveniently carried out in the presence of a catalyst such as dimethylaminopyridine or 4-pyrrolidinopyridine.

The coupling reaction is conveniently carried out in the presence of a suitable base. A suitable base is, for example, an organic amine base such as, for example, pyridine, 2,6-lutidine, collidine, 4-dimethylaminopyridine, triethylamine, di-isopropylethylamine, N-methylmorpholine or diazabicyclo[5.4.0]undec-7-ene, or, for example, an alkali or alkaline earth metal carbonate, for example sodium carbonate, potassium carbonate, cesium carbonate, calcium carbonate, or, for example, an alkali metal hydride, for example sodium hydride.

The reaction is conveniently carried out in the presence of a suitable inert solvent or diluent, for example an ester such as ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one, dimethylsulfoxide or acetonitrile. The reaction is conveniently carried out at a temperature in the range, for example, from 0 to 120° C., particularly at or near ambient temperature.

The compound of Formula II may be used in free base form or in the form of a suitable salt, for example an acid addition salt such as a hydrochloride salt.

By the term "reactive derivative" of the carboxylic acid of Formula III is meant a carboxylic acid derivative that will react with the compound of Formula II to give the corresponding amide. A suitable reactive derivative of a carboxylic acid of the Formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as methanol, ethanol, isopropanol, butanol or N-hydroxybenzotriazole; or an acyl azide, for example an azide formed by the reaction of the acid and azide such as diphenylphosphoryl azide; an acyl cyanide, for example a cyanide formed by the reaction of an acid and a cyanide such as diethylphosphoryl cyanide. A particular reactive derivative of the acid of Formula III is an acyl halide of the Formula IIIa:

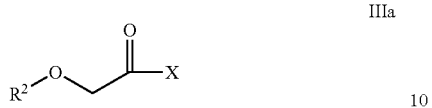

wherein $R^2$ is as hereinbefore defined; X is halogeno, for example chloro; and any functional group in the compound of Formula III is protected if necessary.

The reaction of a reactive derivative of carboxylic acid such as those described above with an amine (such as a compound of the Formula II) is well known in the art. For example a compound of the Formula II may be reacted with an acyl halide of the Formula IIIa in the presence of a base, such as those described above, for example an organic base such as pyridine or 4-dimethylaminopyridine and in a suitable solvent, such as a dipolar aprotic solvent, for example acetonitrile. The reaction may conveniently be performed at a temperature as described above, for example at or near ambient temperature.

When a pharmaceutically-acceptable salt of a quinazoline derivative of the Formula I is required, for example an acid-addition salt, it may be obtained by, for example, reaction of said quinazoline derivative with a suitable acid using a conventional procedure. Methods for the preparation of pharmaceutically acceptable salts are well known in the art and are illustrated in the examples of the present application. For example, following reaction of a quinazoline derivative of the Formula I with an acid, the required acid addition salt may be precipitated from solution by supersaturating the solution containing the quinazoline derivative of the Formula I. Supersaturation may be achieved using well-known techniques, for example by cooling the solution, by removing solvent by evaporation or by the addition of a suitable anti-solvent to precipitate the salt.

To facilitate isolation of a quinazoline derivative of the Formula I during its preparation, the compound may be prepared in the form of a salt that is not a pharmaceutically acceptable salt. The resulting salt can then be modified by conventional techniques to give a pharmaceutically acceptable salt of the compound. Such salt modification techniques are well known and include, for example ion exchange techniques or re-precipitation of the compound from solution in the presence of a pharmaceutically acceptable counter ion as described above, for example by re-precipitation in the presence of a suitable acid such as HCl to give a hydrochloride acid addition salt of a quinazoline derivative of the Formula I.

Preparation of Starting Materials

The compound of the Formula II may be obtained by conventional procedures. For example, as illustrated in Reaction Scheme 1:

Reaction Scheme 1:

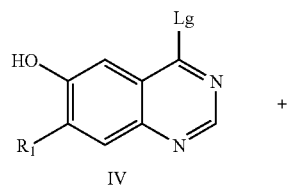

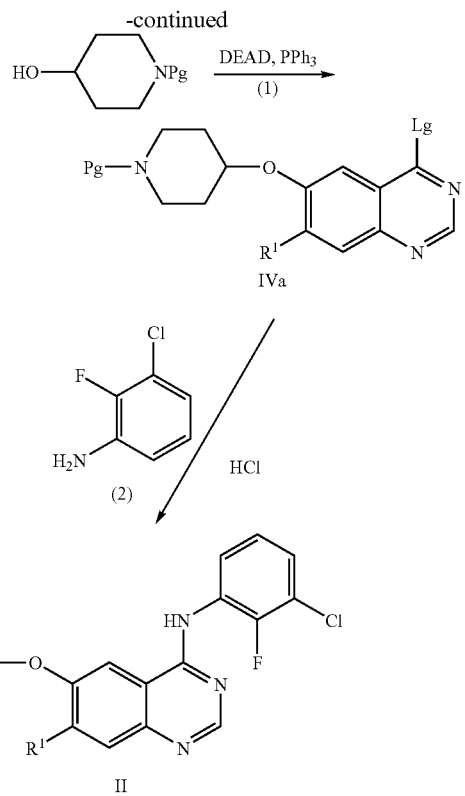

wherein $R^1$ is as hereinbefore defined;
Lg is a displaceable group, for example halogeno such as chloro; and
Pg is a suitable amine protecting group, for example tert-butoxycarbonyl (BOC).

Step (1) Coupling using Mitsunobu coupling reaction. Suitable Mitsunobu conditions include, for example, reaction in the presence of a suitable tertiary phosphine and a di-alkylazodicarboxylate in an organic solvent such as THF, or suitably dichloromethane and in the temperature range 0° C. to 60° C., but suitably at or near ambient temperature. A suitable tertiary phosphine includes for example tri-n-butylphosphine or particularly tri-phenylphosphine. A suitable di-alkylazodicarboxylate includes for example diethyl azodicarboxylate (DEAD) or suitably di-tert-butyl azodicarboxylate. Details of Mitsunobu reactions are contained in Tet. Letts., 31, 699, (1990); The Mitsunobu Reaction, D. L. Hughes, Organic Reactions, 1992, Vol. 42, 335–656 and Progress in the Mitsunobu Reaction, D. L. Hughes, Organic Preparations and Procedures International, 1996, Vol. 28, 127–164.

Step (2)

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one, acetonitrile or dimethylsulfoxide. The reaction is conveniently carried out at a temperature in the range, for example, 10 to 250° C., conveniently in the range 40 to 120° C. or where a solvent or diluent is used at the reflux temperature. Conveniently, the reaction is performed in the presence of a protic solvent such as isopropanol, conveniently in the presence of an acid, for example hydrogen chloride gas in diethyl ether or dioxane, or hydrochloric acid, for example a 4M solution of hydrogen chloride in dioxane, under the conditions described above.

Alternatively, the compound of formula IVa may is reacted with the aniline in the presence of a suitable base. Suitable bases for this reaction are as hereinbefore defined in relation to the reaction of the compounds of formulae II and III. This reaction is conveniently performed in an inert solvent or diluent, and at elevated temperatures. Suitable solvents and reaction conditions are analogous to those described above for Step 2 of the Reaction Scheme 1 described above in which the compound of the formula IVa is reacted with the aniline in the presence of an acid.

In a further process variant, the compound of formula IVa may be reacted directly with the aniline in the absence of an additional acid or base. In this reaction the acid generated by the coupling reaction acts as a catalyst for further reaction.

Compounds of the Formula II may also be prepared according to Reaction Scheme 2:

Pg is a suitable amine protecting group, for example tert-butoxycarbonyl (BOC); and
$Pg^1$ is a suitable hydroxy protecting group, for example an acyl group such as acetyl.

Step 1:
When Lg is halogeno, such as chloro, the compound of the formula V is reacted with a suitable halogenating agent, for example thionyl chloride or a halogenated phosphorus derivative such as phosphorus oxychloride or phosphorus pentachloride. The halogenation reaction is conveniently carried out in the presence of a suitable base. Suitable bases are as hereinbefore defined in relation to the reaction of the compounds of formulae II and III, for example an organic amine base such a di-isopropylamine. The reaction is suitable carried out is a suitable inert solvent, for example an aromatic solvent such as toluene. The reaction is suitably carried out at an elevated temperature, for example at a temperature of from 30 to 120° C., preferably from 60 to 90° C.

Step 2
Analogous conditions to those used in Step 2 in Reaction Scheme 1. Conveniently, the compound of the formula Vb

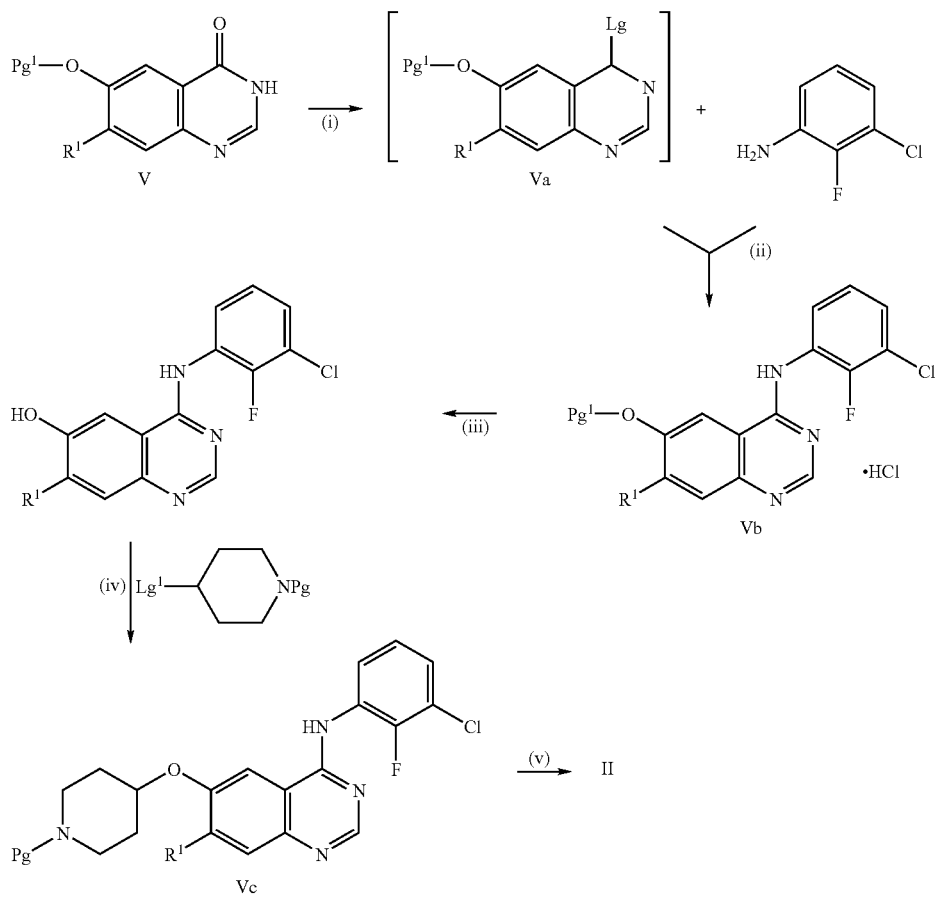

Reaction Scheme 2:

wherein:
$R^1$ is as hereinbefore defined;
Lg is a suitable displaceable group, for example halogeno such as chloro;
$Lg^1$ is a suitable displaceable group;

may be prepared directly from the compound of formula V without isolating the compound of formula Va. In this process variant, the aniline is added directly to the reaction mixture following introduction of the displaceable group Lg, to the compound of formula V.

Step 3

Removal of the hydroxy protecting group using conventional techniques. For example, when $Pg^1$ is an acyl group by hydrolysis with a suitable base such as an alkali metal hydroxide, for example lithium, sodium hydroxide or ammonia.

step 4

Suitable displaceable groups represented by $Lg^1$ include, for example halogeno, alkanesulfonyloxy or arylsulfonyloxy. A particular $Lg^1$ group is selected from chloro, bromo, methanesulfonyloxy, 4-nitrobenzenesulfonyloxy and toluene-4-sulfonyloxy, more particularly $Lg^1$ is selected from methanesulfonyloxy, 4-nitrobenzenesulfonyloxy and toluene-4-sulfonyloxy.

The reaction is advantageously carried out in the presence of base. Suitable bases are those defined herein in relation to the reaction of the compounds of formulae II and III, for example, an alkali metal or alkaline earth metal carbonate such as sodium carbonate, potassium carbonate, cesium carbonate or calcium carbonate or alkali metal hydroxide, for example sodium hydroxide. The reaction is suitably effected in the presence of an inert solvent or diluent, for example an alkanol or ester such as methanol, ethanol, 2-propanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or (suitably) a dipolar aprotic solvent such as N,N-dimethylformamide, N,N-dimethylacetamide, N-methylpyrrolidin-2-one or dimethylsulfoxide. The reaction is conveniently effected at a temperature in the range, for example, 10 to 150° C. (or the boiling point of the solvent), suitably in the range 70 to 110° C.

Step 5

Removal of the amine protecting group, Pg, using conventional methods. For example when Pg is a BOC group by treating the compound of the formula Vc with a suitable acid such as hydrochloric acid.

The starting materials used in Reaction Schemes 1 and 2 are known or can be prepared using known processes for the preparation of analogous compounds. Examples of suitable methods for the preparation of starting materials and intermediates are illustrated below in the Examples.

In the process section above and hereafter, the expression "inert solvent" refers to a solvent which does not react with the starting materials, reagents, intermediates or products in a manner which adversely affects the yield of the desired product.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

Biological Assays

The following assays may be used to measure the effects of the compounds of the present invention as inhibitors of the erbB tyrosine kinases, as inhibitors in-vitro of the proliferation of KB cells (human naso-pharangeal carcinoma cells) and as inhibitors in vivo on the growth in nude mice of xenografts of LoVo tumour cells (colorectal adenocarcinoma).

a) Protein Tyrosine Kinase Phosphorylation Assays

This test measures the ability of a test compound to inhibit the phosphorylation of a tyrosine containing polypeptide substrate by an erbB tyrosine kinase enzyme.

Recombinant intracellular fragments of EGFR, erbB2 and erbB4 (accession numbers X00588, X03363 and L07868 respectively) were cloned and expressed in the baculovirus/Sf21 system. Lysates were prepared from these cells by treatment with ice-cold lysis buffer (20 mM N-2-hydroxyethylpiperizine-N'-2-ethanesulfonic acid (HEPES) pH7.5, 150 mM NaCl, 10% glycerol, 1% Triton X-100, 1.5 mM $MgCl_2$, 1 mM ethylene glycol-bis($\beta$-aminoethyl ether) N',N',N',N'-tetraacetic acid (EGTA), plus protease inhibitors and then cleared by centrifugation.

Constitutive kinase activity of the recombinant protein was determined by its ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 μg of peptide in a 100 μl phosphate buffered saline (PBS) solution and incubated at 4° C. overnight). Plates were washed in PBS-T (phosphate buffered saline with 0.5% Tween 20) then in 50 mM HEPES pH 7.4 at room temperature to remove any excess unbound synthetic peptide. EGFR, ErbB2 or ErbB4 tyrosine kinase activity was assessed by incubation in peptide coated plates for 20 minutes at 22° C. in 100 mM HEPES pH 7.4, adenosine trisphosphate (ATP) at Km concentration for the respective enzyme, 10 mM $MnCl_2$, 0.1 mM $Na_3VO_4$, 0.2 mM DL-dithiothreitol (DTT), 0.1% Triton X-100 with test compound in DMSO (final concentration of 2.5%). Reactions were terminated by the removal of the liquid components of the assay followed by washing of the plates with PBS-T.

The immobilised phospho-peptide product of the reaction was detected by immunological methods. Firstly, plates were incubated for 90 minutes at room temperature with anti-phosphotyrosine primary antibodies that were raised in the mouse (4G10 from Upstate Biotechnology). Following extensive washing, plates were treated with Horseradish Peroxidase (HRP) conjugated sheep anti-mouse secondary antibody (NXA931 from Amersham) for 60 minutes at room temperature. After further washing, HRP activity in each well of the plate was measured colorimetrically using 22'-Azino-di-[3-ethylbenzthiazoline sulfonate (6)]diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) EGFR Driven KB Cell Proliferation Assay

This assay measures the ability of a test compound to inhibit the proliferation of KB cells (human naso-pharangeal carcinoma obtained from the American Type Culture Collection (ATCC)).

KB cells were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA).

Cell density was measured using a haemocytometer and viability was calculated using trypan blue solution before being seeded at a density of $1.25 \times 10^3$ cells per well of a 96 well plate in DMEM containing 2.5% charcoal stripped serum, 1 mM glutamine and non-essential amino acids at 37° C. in 7.5% $CO_2$ and allowed to settle for 4 hours.

Following adhesion to the plate, the cells are treated with or without EGF (final concentration of 1 ng/ml) and with or without compound at a range of concentrations in dimethylsulfoxide (DMSO) (0.1% final) before incubation for 4 days. Following the incubation period, cell numbers were determined by addition of 50 μl of 3-(4,5-Dimethylthiazol-2-yl)-2,5-diphenyltetrazolium bromide (MTT) (stock 5 mg/ml) for 2 hours. MTT solution was then tipped off, the plate gently tapped dry and the cells dissolved upon the addition of 100 μl of DMSO.

Absorbance of the solubilised cells was read at 540 nm using a Molecular Devices ThermoMax microplate reader. Inhibition of proliferation was expressed as an $IC_{50}$ value. This was determined by calculation of the concentration of compound that was required to give 50% inhibition of proliferation. The range of proliferation was calculated from the positive (vehicle plus EGF) and negative (vehicle minus EGF) control values.

c) Clone 24 Phospho-erbB2 Cell Assay

This immunofluorescence end point assay measures the ability of a test compound to inhibit the phosphorylation of erbB2 in a MCF7 (breast carcinoma) derived cell line which was generated by transfecting MCF7 cells with the full length erbB2 gene using standard methods to give a cell line that overexpresses full length wild type erbB2 protein (hereinafter 'Clone 24' cells).

Clone 24 cells were cultured in Growth Medium (phenol red free Dulbecco's modified Eagle's medium (DMEM) containing 10% foetal bovine serum, 2 mM glutamine and 1.2 mg/ml G418) in a 7.5% $CO_2$ air incubator at 37° C. Cells were harvested from T75 stock flasks by washing once in PBS (phosphate buffered saline, pH7.4, Gibco No. 10010-015) and harvested using 2 mls of Trypsin (1.25 mg/ml)/ethylaminediaminetetraacetic acid (EDTA) (0.8 mg/ml) solution. The cells were resuspended in Growth Medium. Cell density was measured using a haemocytometer and viability was calculated using Trypan Blue solution before being further diluted in Growth Medium and seeded at a density of $1 \times 10^4$ cells per well (in 100 ul) into clear bottomed 96 well plates (Packard, No. 6005182).

3 days later, Growth Medium was removed from the wells and replaced with 100 ul Assay Medium (phenol red free DMEM, 2 mM glutamine, 1.2 mg/ml G418) either with or without erbB inhibitor compound. Plates were returned to the incubator for 4 hrs and then 20 μl of 20% fomaldehdye solution in PBS was added to each well and the plate was left at room temperature for 30 minutes. This fixative solution was removed with a multichannel pipette, 100 μl of PBS was added to each well and then removed with a multichannel pipette and then 50 μl PBS was added to each well. Plates were then sealed and stored for up to 2 weeks at 4° C.

Immunostaining was performed at room temperature. Wells were washed once with 200 μl PBS/Tween 20 (made by adding 1 sachet of PBS/Tween dry powder (Sigma, No. P3563) to 1 L of double distilled $H_2O$) using a plate washer then 200 μl Blocking Solution (5% Marvel dried skimmed milk (Nestle) in PBS/Tween 20) was added and incubated for 10 minutes. Blocking Solution was removed using a plate washer and 200 μl of 0.5% Triton X-100/PBS was added to permeabalise the cells. After 10 minutes, the plate was washed with 200 μl PBS/Tween 20 and then 200 μl Blocking Solution was added once again and incubated for 15 minutes. Following removal of the Blocking Solution with a plate washer, 30 μl of rabbit polyclonal anti-phospho ErbB2 IgG antibody (epitope phospho-Tyr 1248, SantaCruz, No. SC-12352-R), diluted 1:250 in Blocking Solution, was added to each well and incubated for 2 hours. Then this primary antibody solution was removed from the wells using a plate washer followed by two 200 μl PBS/Tween 20 washes using a plate washer. Then 30 μl of Alexa-Fluor 488 goat anti-rabbit IgG secondary antibody (Molecular Probes, No. A-11008), diluted 1:750 in Blocking Solution, was added to each well. From now onwards, wherever possible, plates were protected from light exposure, at this stage by sealing with black backing tape. The plates were incubated for 45 minutes and then the secondary antibody solution was removed from the wells followed by two 200 ul PBS/Tween 20 washes using a plate washer. Then 100 μl PBS was added to each plate, incubated for 10 minutes and then removed using a plate washer. Then a further 100 μl PBS was added to each plate and then, without prolonged incubation, removed using a plate washer. Then 50 μl of PBS was added to each well and plates were resealed with black backing tape and stored for up to 2 days at 4° C. before analysis.

The Fluorescence signal is each well was measured using an Acumen Explorer Instrument (Acumen Bioscience Ltd.), a plate reader that can be used to rapidly quantitate features of images generated by laser-scanning. The instrument was set to measure the number of fluorescent objects above a pre-set threshold value and this provided a measure of the phosphorylation status of erbB2 protein. Fluorescence dose response data obtained with each compound was exported into a suitable software package (such as Origin) to perform curve fitting analysis. Inhibition of erbB2 phosphorylation was expressed as an $IC_{50}$ value. This was determined by calculation of the concentration of compound that was required to give 50% inhibition of erbB2 phosphorylation signal.

d) In vivo Xenograft Assay

This assay measures the ability of a test compound to inhibit the growth of a LoVo tumour (colorectal adenocarcinoma obtained from the ATCC) in Female Swiss athymic mice (Alderley Park, nu/nu genotype).

Female Swiss athymic (nu/nu genotype) mice were bred and maintained in Alderley Park in negative pressure Isolators (PFI Systems Ltd.). Mice were housed in a barrier facility with 12 hr light/dark cycles and provided with sterilised food and water ad libitum. All procedures were performed on mice of at least 8 weeks of age. LoVo tumour cell (colorectal adenocarcinoma obtained from the ATCC) xenografts were established in the hind flank of donor mice by sub cutaneous injections of $1 \times 10^7$ freshly cultured cells in 100 μl of serum free media per animal. On day 5 post-implant, mice were randomised into groups of 7 prior to the treatment with compound or vehicle control that was administered once daily at 0.1 ml/10 g body weight. Tumour volume was assessed twice weekly by bilateral Vernier calliper measurement, using the formula (length×width)×√(length×width)×(π/6), where length was the longest diameter across the tumour, and width was the corresponding perpendicular. Growth inhibition from start of study was calculated by comparison of the mean changes in tumour volume for the control and treated groups, and statistical significance between the two groups was evaluated using a Students t test.

e) hERG-Encoded Potassium Channel Inhibition Assay

This assay determines the ability of a test compound to inhibit the tail current flowing through the human ether-a-go-go-related-gene (hERG)-encoded potassium channel.

Human embryonic kidney (HEK) cells expressing the hERG-encoded channel were grown in Minimum Essential Medium Eagle (EMEM; Sigma-Aldrich catalogue number M2279), supplemented with 10% Foetal Calf Serum (Labtech International; product number 4-101-500), 10% M1 serum-free supplement (Egg Technologies; product number 70916) and 0.4 mg/ml Geneticin G418 (Sigma-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (see below) at room temperature (~20° C.). This chamber was fixed to the stage of an inverted, phase-contrast microscope. Immediately after placing the coverslip in the chamber, bath solution was perfused into the chamber from a gravity-fed reservoir for 2 minutes at a rate of ~2 ml/min. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of −80 mV (set by the amplifier), and appropriate adjustment of series resistance and capacitance controls, electrophysiology software (Clampex, Axon Instruments) was used to set a holding potential (−80 mV) and to deliver a voltage protocol. This protocol was applied every 15 seconds and consisted of a 1 s step to +40 mV followed by a 1 s step to −50 mV. The current response to each imposed voltage protocol was low pass filtered by the amplifier at 1 kHz. The filtered signal was then acquired, on line, by digitising this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
|---|---|---|
| NaCl | — | 137 |
| KCl | 130 | 4 |
| MgCl$_2$ | 1 | 1 |
| CaCl$_2$ | — | 1.8 |
| HEPES | 10 | 10 |
| glucose | — | 10 |
| Na$_2$ATP | 5 | — |
| EGTA | 5 | — |

| Parameter | Pipette | Bath |
|---|---|---|
| pH | 7.18–7.22 | 7.40 |
| pH adjustment with | 1M KOH | 1M NaOH |
| Osmolarity (mOsm) | 275–285 | 285–295 |

The amplitude of the hERG-encoded potassium channel tail current following the step from +40 mV to −50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a percentage of that in the presence of vehicle.

Test compound potency (IC$_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

Although the pharmacological properties of the compounds of the Formula I vary with structural change as expected, in general activity possessed by compounds of the Formula I, may be demonstrated at the following concentrations or doses in one or more of the above tests (a), (b), (c) and (d):

Test (a):- IC$_{50}$ in the range, for example, 0.001–0.1 µM;
Test (b):- IC$_{50}$ in the range, for example, 0.001–0.1 µM;
Test (c):- IC$_{50}$ in the range, for example, 0.1–10 µM;
Test (d):- activity in the range, for example, 1–200 mg/kg/day;

No physiologically unacceptable toxicity was observed in Test (d) at the effective dose for compounds tested of the present invention. Accordingly no untoward toxicological effects are expected when a compound of Formula I, or a pharmaceutically-acceptable salt thereof, as defined hereinbefore is administered at the dosage ranges defined hereinafter.

By way of example, using Test (a) for the inhibition of EGFR tyrosine kinase protein phosphorylation and Test (a) for the inhibition of erbB2 tyrosine kinase protein phosphorylation described above, the compound described in Example 1 herein gave the IC$_{50}$ results shown below in Table A:

TABLE A

| Compound of Example | IC$_{50}$ (nM) Test (a) (Inhibition of EGFR tyrosine kinase protein phosphorylation) | IC$_{50}$ (nM) Test (a) (Inhibition of erbB2 tyrosine kinase protein phosphorylation) |
|---|---|---|
| 1 | 3 | 59 |

According to a further aspect of the invention there is provided a pharmaceutical composition which comprises a quinazoline derivative of the Formula I, or a pharmaceutically-acceptable salt, or a pharmaceutically acceptable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a quinazoline derivative of the Formula I will naturally vary according to the nature and severity of the conditions, the age and sex of the animal or patient and the route of administration, according to well known principles of medicine.

In using a quinazoline derivative of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

We have found that the compounds of the present invention possess anti-proliferative properties such as anti-cancer properties that are believed to arise from their erbB family receptor tyrosine kinase inhibitory activity, particularly inhibition of the EGF receptor (erbB 1) tyrosine kinase. Furthermore, certain of the compounds according to the present invention possess substantially better potency against the EGF receptor tyrosine kinase, than against other tyrosine kinase enzymes, for example erbB2. Such compounds possess sufficient potency against the EGF receptor tyrosine kinase that they may be used in an amount sufficient to inhibit EGF receptor tyrosine kinase whilst demonstrating little, or significantly lower, activity against other tyrosine kinase enzymes such as erbB2. Such compounds are likely to be useful for the selective inhibition of EGF receptor tyrosine kinase and are likely to be useful for the effective treatment of, for example EGF driven tumours.

Accordingly, the compounds of the present invention are expected to be useful in the treatment of diseases or medical conditions mediated alone or in part by erbB receptor tyrosine kinases (especially EGF receptor tyrosine kinase), i.e. the compounds may be used to produce an erbB receptor tyrosine kinase inhibitory effect in a warm-blooded animal in need of such treatment. Thus the compounds of the present invention provide a method for the treatment of malignant cells characterised by inhibition of one or more of the erbB family of receptor tyrosine kinases. Particularly the compounds of the invention may be used to produce an anti-proliferative and/or pro-apoptotic and/or anti-invasive effect mediated alone or in part by the inhibition of erbB receptor tyrosine kinases. Particularly, the compounds of the present invention are expected to be useful in the prevention or treatment of those tumours that are sensitive to inhibition of one or more of the erbB receptor tyrosine kinases, such as EGF and/or erbB2 and/or erbB4 receptor tyrosine kinases (especially EGF receptor tyrosine kinase) that are involved in the signal transduction steps which drive proliferation and survival of these tumour cells. Accordingly the compounds of the present invention are expected to be useful in the treatment of psoriasis, benign prostatic hyperplasia (BPH), atherosclerosis and restenosis and/or cancer by providing an anti-proliferative effect, particularly in the treatment of erbB receptor tyrosine kinase sensitive cancers. Such benign or malignant tumours may affect any tissue and include non-solid tumours such as leukaemia, multiple myeloma or lymphoma, and also solid tumours, for example bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancers.

According to this aspect of the invention there is provided a quinazoline derivative of the Formula I, or a pharmaceutically acceptable salt, or pharmaceutically acceptable ester thereof, for use as a medicament.

According to a further aspect of the invention there is provided a compound of the Formula I, or a pharmaceutically acceptable salt, or a pharmaceutically acceptable ester thereof, for use in the production of an anti-proliferative effect in a warm-blooded animal such as man.

Thus according to this aspect of the invention there is provided the use of a quinazoline derivative of the Formula I, or a pharmaceutically-acceptable salt, or a pharmaceutically acceptable ester thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative of the Formula I, or a pharmaceutically acceptable salt, or a pharmaceutically acceptable ester thereof, as hereinbefore defined.

According to a further aspect of the invention there is provided the use of a quinazoline derivative of the Formula I, or a pharmaceutically-acceptable salt, or a pharmaceutically acceptable ester salt thereof, as defined hereinbefore in the manufacture of a medicament for use in the prevention or treatment of those tumours which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further feature of this aspect of the invention there is provided a method for the prevention or treatment of those tumours which are sensitive to inhibition of one or more of the erbB family of receptor tyrosine kinases, such as EGFR and/or erbB2 and/or erbB4 (especially EGFR), that are involved in the signal transduction steps which lead to the proliferation and/or survival of tumour cells, in a warm-blooded animal, such as man, in need of such treatment which comprises administering to said animal an effective amount of a quinazoline derivative of the Formula I, or a pharmaceutically-acceptable salt, or a pharmaceutically acceptable ester thereof, as defined hereinbefore.

According to a further feature of this aspect of the invention there is provided a compound of the Formula I, or a pharmaceutically acceptable salt, or a pharmaceutically acceptable ester thereof, for use in the prevention or treatment of those tumours which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further aspect of the invention there is provided the use of a quinazoline derivative of the Formula I, or a pharmaceutically-acceptable salt, or a pharmaceutically acceptable ester thereof, as defined hereinbefore in the manufacture of a medicament for use in providing a EGFR and/or erbB2 and/or erbB4 (especially a EGFR) tyrosine kinase inhibitory effect.

According to a further feature of this aspect of the invention there is provided a method for providing a EGFR and/or an erbB2 and or an erbB4 (especially a EGFR) tyrosine kinase inhibitory effect in a warm-blooded animal, such as man, in need thereof, which comprises administering to said animal an effective amount of a quinazoline derivative of the Formula I, or a pharmaceutically-acceptable salt, or a pharmaceutically acceptable ester thereof, as defined hereinbefore.

According to a further feature of this aspect of the invention there is provided a compound of the Formula I, or a pharmaceutically acceptable salt, or a pharmaceutically acceptable ester thereof, for use in providing a EGFR and/or erbB2 and/or erbB4 (especially a EGFR) tyrosine kinase inhibitory effect.

According to a further feature of the present invention there is provided the use of a quinazoline derivative of the Formula I, or a pharmaceutically-acceptable salt, or a pharmaceutically acceptable ester thereof, as defined hereinbefore in the manufacture of a medicament for use in providing a selective EGFR tyrosine kinase inhibitory effect.

According to a further feature of this aspect of the invention there is provided a method for providing a selective EGFR tyrosine kinase inhibitory effect in a warm-blooded animal, such as man, in need thereof which comprises administering to said animal an effective amount of a quinazoline derivative of the Formula I, or a pharmaceutically-acceptable salt, or a pharmaceutically acceptable ester thereof, as defined hereinbefore.

According to a further feature of this aspect of the invention there is provided a compound of the Formula I, or a pharmaceutically acceptable salt, or a pharmaceutically acceptable ester thereof, for use in providing a selective EGFR tyrosine kinase inhibitory effect.

By "a selective EGFR kinase inhibitory effect" is meant that the quinazoline derivative of Formula I is more potent against EGF receptor tyrosine kinase than it is against other kinases. In particular some of the compounds according to the invention are more potent against EGF receptor kinase than it is against other tyrosine kinases such as other erbB receptor tyrosine kinases particularly erbB2. For example a selective EGFR kinase inhibitor according to the invention is at least 5 times, preferably at least 10 times more potent against EGF receptor tyrosine kinase than it is against erbB2 tyrosine kinase, as determined from the relative $IC_{50}$ values in suitable assays (for example the by comparing the $IC_{50}$ value from the KB cell assay with the $IC_{50}$ value from the Clone 24 phospho-erbB2 cell assay for a given test compound as described above).

According to a further aspect of the present invention there is provided the use of a quinazoline derivative of the Formula I, or a pharmaceutically-acceptable salt, or a pharmaceutically acceptable ester thereof, as defined hereinbefore in the manufacture of a medicament for use in the treatment of a cancer (for example a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

According to a further feature of this aspect of the invention there is provided a method for treating a cancer (for example a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer) in a warm-blooded animal, such as man, in need of such treatment, which comprises administering to said animal an effective amount of a quinazoline derivative of the Formula I, or a pharmaceutically-acceptable salt, or a pharmaceutically acceptable ester thereof, as defined hereinbefore.

According to a further aspect of the invention there is provided a quinazoline derivative of the Formula I, or a pharmaceutically acceptable salt, or a pharmaceutically acceptable ester thereof, for use in the treatment of a cancer (for example selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

As mentioned above the size of the dose required for the therapeutic or prophlyactic treatment of a particular disease will necessarily be varied depending upon, amongst other things, the host treated, the route of administration and the severity of the illness being treated.

The anti-proliferative treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example other inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the Formula I as defined hereinbefore and an additional anti-tumour agent as defined hereinbefore for the conjoint treatment of cancer.

Although the quinazoline derivatives of the Formula I are primarily of value as therapeutic agents for use in warm-blooded animals (including man), they are also useful whenever it is required to inhibit the effects of the erbB receptor tyrosine protein kinases. Thus, they are useful as pharmacological standards for use in the development of new biological tests and in the search for new pharmacological agents.

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 Pascals; 4.5–30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and/or analytical LCMS, and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; b, broad;

(viii) chemical symbols have their usual meanings; SI units and symbols are used;

(ix) solvent ratios are given in volume:volume (v/v) terms; and (x) mass spectra (MS) were run with an electron energy of 70 electron volts in the chemical ionization (CI) mode using a direct exposure probe and ionization was effected by electrospray; values for m/z are given; generally, only ions which indicate the parent mass are reported; and unless otherwise stated, the mass ion quoted is $(MH)^+$;

(xi) where a synthesis is described as being analogous to that described in a previous example the amounts used are the millimolar ratio equivalents to those used in the previous example;
(xii) melting points are uncorrected and were determined using a Mettler SP62 automatic melting point apparatus or Buchi 535 melting point apparatus; and
(xiii) the following abbreviations have been used:

| | |
|---|---|
| DMA | N,N-dimethylacetamide |
| HATU | O-(7-azabenzotriazol-1-yl)-N,N,N',N'-tetramethyluronium hexafluorophosphate |
| IMS | Industrial methylated spirits |
| IPA | Isopropyl alcohol |
| MeOH | Methanol; and |
| NMP | N-methylpyrrolidin-2-one |

EXAMPLE 1

4-(3-chloro-2-fluoroanilino)-6-[1-(hydroxyacetyl)piperidin-4-yloxy]-7-methoxyquinazoline

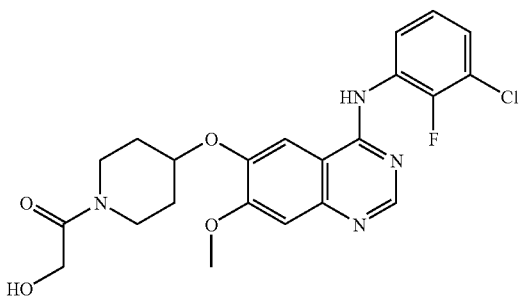

HATU (28.9 g) was added to a stirred solution of 4-(3-chloro-2-fluoroanilino)-7-methoxy-6-(piperidin-4-yloxy)quinazoline dihydrochloride (30 g), glycolic acid (5.40 g) and di-isopropylethylamine (44.70 ml) in methylene chloride (900 ml). After 1.5 hours the reaction mixture was washed with sodium hydroxide solution (2M), water and saturated brine. The resulting product was then purified by flash chromatography on silica eluting with 3% MeOH/methylene chloride. The fractions containing the desired product were combined and reduced in vacuo to give the title product as a white solid which was recrystallised from acetonitrile (29.6 g); NMR Spectrum: (DMSO $d_6$) 1.65–1.81 (m, 2H), 1.99–2.10 (m, 2H), 3.26–3.34 (m, 1H), 3.37–3.47 (m, 1H), 3.60–3.68 (m, 1H), 3.81–3.89 (m, 1H), 3.95 (s, 3H), 4.14 (d, 2H), 4.50 (t, 1H), 4.78 (m, 1H), 7.25 (s, 1H), 7.30 (t, 1H), 7.46–7.55 (m, 2H), 7.88 (s, 1H), 8.40 (s, 1H), 9.55 (s, 1H); Mass Spectrum: $(M+H)^+$ 460.94.

The 4-(3-chloro-2-fluoroanilino)-7-methoxy-6-(piperidin-4-yloxy)quinazoline dihydrochloride starting material was prepared as follows:

6-Acetoxy-4-chloro-7-methoxyquinazoline, (Example 25-5 in WO01/66099; 10.0 g, 39.6 mmole) was added in portions to a stirred 7N methanolic ammonia solution (220 ml) cooled to 10° C. in an ice/water bath. After stirring for one hour the precipitate was filtered, washed with diethylether and dried thoroughly under high vacuum to give 4-chloro-6-hydroxy-7-methoxyquinazoline (5.65 g, 67.8%); NMR Spectrum: (DMSO $d_6$) 3.96 (s, 3H); 7.25 (s, 1H); 7.31 (s, 1H); 8.68 (s, 1H); Mass Spectrum: $(M+H)^+$ 211.

Di-tert-butylazodicarboxylate (9.22 g) in methylene chloride (20 ml) was added slowly to a stirred suspension of 4-chloro-6-hydroxy-7-methoxyquinazoline (5.63 g), 4-hydroxy-1-tert-butoxycarbonylpiperidine (8.06 g) and triphenylphosphine (10.5 g) in methylene chloride (100 ml) at 5° C. under an atmosphere of nitrogen. The reaction mixture was allowed to warm to room temperature for 16 hours. The reaction mixture was then evaporated under vacuum and adsorbed onto silica and the product was eluted with iso-hexane/ethyl acetate/triethylamine (75/24/1 followed by 70/29/1). The fractions containing the desired product were combined and evaporated under vacuum to give tert-butyl 4-[(4-chloro-7-methoxyquinazolin-6-yl)oxy]piperidine-1-carboxylate as a white solid (10.3 g); $^1$H NMR Spectrum: (DMSO $d_6$) 1.40 (s, 9H), 1.56–1.69 (m, 2H), 1.93–2.04 (m, 2H), 3.20–3.31 (m, 2H), 3.60–3.70 (m, 2H), 4.00 (s, 3H), 4.89 (m, 1H), 7.45 (s, 1H), 7.50 (s, 1H), 8.86 (s, 1H); Mass Spectrum: $(M+H)^{30}$ 394.

4.0M HCl in Dioxane (4.0 ml) was added to a suspension of tert-butyl 4-[(4-chloro-7-methoxyquinazolin-6-yl)oxy]piperidine-1-carboxylate (2.62 g) and 3-chloro-2-fluoroaniline (1.08 g) in iso-propanol (50 ml). The reaction mixture was stirred and heated at 100° C. for 2 hours. The yellow precipitate was filtered hot and washed with iso-propanol followed by diethylether and dried under vacuum to give 6-(piperidin-4-yloxy)-4-(3-chloro-2-fluoroanilino)-7-methoxyquinazoline as a di-hydrochloride salt (2.38 g); $^1$H NMR Spectrum: (DMSO $d_6$) 1.84–1.99 (m, 2H), 2.22–2.33 (m, 2H), 3.12–3.33 (m, 4H), 4.00 (s, 3H), 5.08 (m, 1H), 7.34 (t, 1H), 7.40 (s, 1H), 7.50 (t, 1H), 7.62 (t, 1H), 8.80 (s, 1H), 8.84–8.94 (m, 2H), 8.99–9.11 (m, 1H); Mass Spectrum: $(M+H)^+$ 403.

EXAMPLE 2

4-(3-Chloro-2-fluoroanilino)-6-[1-(hydroxyacetyl)piperidin-4-yloxy]-7-methoxyquinazoline L-Tartarate Dihydrate Salt A solution of L-tartaric acid (0.85 g) in water (5 ml) was added to 4-(3-chloro-2-fluoroanilino)-6-[1-(hydroxyacetyl)piperidin-4-yloxy]-7-methoxyquinazoline (2.5 g) in IMS (25 ml) at 80° C. After stirring at 80° C. for 5 minutes, the solution was cooled to ambient temperature over 1 hour. At around 45° C., a solid crystallised. The mixture was stirred at ambient temperature for 30 minutes before cooling to 0–5° C. The solid was filtered and washed with IMS (2×7.5 ml). The solid was dried at 50° C. under vacuum to constant weight to give the title product (3.13 g; 89.3% yield). NMR Spectrum: (DMSO $d_6$) 1.63–1.81 (m, 2H); 1.98–2.11 (m, 2H); 3.28–3.45 (m, 2H); 3.59–3.67 (m, 1H); 3.83–3.90 (m, 1H); 3.95 (s, 3H); 4.14 (s, 2H); 4.32 (s, 2H); 4.55 (bs, 1H), 4.77 (m, 1H); 7.24 (s, 1H); 7.29 (t, 1H); 7.47–7.56 (m, 2H); 7.89 (s, 1H); 8.39 (s, 1H) 9.62 (bs, 1H); Melting Point: Onset 128.8° C., peak 137.4° C.

EXAMPLE 3

4-(3-Chloro-2-fluoroanilino)-6-[1-(hydroxyacetyl)piperidin-4-yloxy]-7-methoxyquinazoline Maleate Salt A solution of maleic acid (0.66 g) in IMS (10 ml) was added to 4-(3-chloro-2-fluoroanilino)-6-[1-(hydroxyacetyl)piperidin-4-yloxy]-7-methoxyquinazoline (2.5 g) in IMS (25 ml) at 80° C. Water (3 ml) was added. After stirring at 80° C. for 5 minutes, the solution was cooled to ambient temperature over 1 hour. At approximately 50° C., a solid crystallised. The mixture was stirred at ambient temperature for 30 minutes before cooling to 0–5° C. The solid was filtered and washed with IMS (2×7.5 ml). The solid was dried at 50° C. under vacuum to constant weight. The solid was then heated in 10% aqueous IPA at 82–85° C. for 1 hour before cooling to ambient temperature over 1 hour. The solid was filtered and washed with IPA (2×5 ml). The solid was dried at 50° C. under vacuum to constant weight to give the title product (1.63 g; 52.3% yield); NMR Spectrum: (DMSO $d_6$) 1.63–1.82 (m, 2H); 2.00–2.10 (m, 2H); 3.28–3.45 (m, 2H); 3.59–3.67 (m, 1H); 3.83–3.90 (m, 1H); 3.98 (s, 3H); 4.14 (s, 2H); 4.79 (m, 1H); 6.19 (s, 2H); 7.25 (s, 1H); 7.33 (t, 1H); 7.52–7.59 (m, 2H); 7.95 (s, 1H); 8.54 (s, 1H) 10.14 (bs, 1H); Melting Point: Onset 165.4° C., peak 169.7° C.

EXAMPLE 4

4-(3-Chloro-2-fluoroanilino)-6-[1-(hydroxyacetyl) piperidin-4-yloxy]-7-methoxyquinazoline Methanesulfonate Salt

EXAMPLE 4.1

A solution of methanesulfonic acid (1.02 g) in water (7 ml) was added to 4-(3-chloro-2-fluoroanilino)-6-[1-(hydroxyacetyl)piperidin-4-yloxy]-7-methoxyquinazoline (4.6 g) in IPA (25 ml) at 40° C. The mixture was heated to 80° C. during which all solids dissolved. The solution was filtered into a clean vessel maintaining the solution above 50° C. After a line wash of 15% aqueous IPA (18 ml), the combined filtrates and wash were heated at 40° C. On stirring, a solid crystallised. The mixture was cooled to ambient temperature over 30 minutes, stirred at this temperature for 1 hour. The solid was filtered, washed with IPA (2×7 ml) and dried at 50° C. under vacuum to constant weight to give 4-(3-Chloro-2-fluoroanilino)-6-[1-(hydroxyacetyl)piperidin-4-yloxy]-7-methoxyquinazoline methanesulfonate salt (4.66 g; 83% yield); NMR Spectrum: (DMSO $d_6$) 1.63–1.81 (m, 2H); 2.00–2.14 (m, 2H); 2.34 (s, 3H); 3.30–3.48 (m, 2H); 3.57–3.69 (m, 1H); 3.80–3.90 (m, 1H); 4.03 (s, 3H); 4.14 (s, 2H); 4.47 (m, 1H); 7.36 (s, 1H); 7.40 (t, 1H); 7.59 (t, 1H); 7.68 (t, 1H); 8.11 (s, 1H); 8.85 (s, 1H) 11.24 (bs, 1H); Melting Point: Onset 228.9° C., peak 232° C.

EXAMPLE 4.2

4-(3-Chloro-2-fluoroanilino)-6-[1-(hydroxyacetyl)piperidin-4-yloxy]-7-methoxyquinazoline (25 g) was dissolved in NMP (125 ml) by heating to 35–40° C. The resultant solution was filtered to a clean vessel maintaining the temperature at 35–40° C. After a line wash of NMP (25 ml), methanesulfonic acid (5.48 g) was added followed by IMS (150 ml). The mixture is cooled to ambient temperature over 2 hours during which the methanesulfonate salt crystallises. The reaction mixture is further cooled to 0–5° C. The solid was filtered, washed with IMS (2×50 ml) and dried at 55° C. under vacuum to constant weight to give 4-(3-Chloro-2-fluoroanilino)-6-[1-(hydroxyacetyl)piperidin-4-yloxy]-7-methoxyquinazoline methanesulfonate salt (26.48 g; 87.6% yield); NMR Spectrum: (DMSO $d_6$) 1.62–1.81 (m, 2H); 2.00–2.15 (m, 2H); 2.36 (s, 3H); 3.29–3.48 (m, 2H); 3.57–3.68 (m, 1H); 3.80–3.90 (m, 1H); 4.03 (s, 3H); 4.14 (s, 2H); 4.89 (m, 1H); 7.38 (s, 1H); 7.40 (t, 1H); 7.60 (t, 1H); 7.68 (t, 1H); 8.12 (s, 1H); 8.86 (s, 1H) 11.24 (bs, 1H); Melting Point: Onset 230.5° C., peak 232° C.

EXAMPLE 5

4-(3-Chloro-2-fluoroanilino)-6-[1-(hydroxyacetyl) piperidin-4-yloxy]-7-methoxyquinazoline 4-(3-Chloro-2-fluoroanilino)-7-methoxy-6-(piperidin-4-yloxy)-quinazoline dihydrochloride ethanol solvate (91.8 g), 4-(dimethylamino)pyridine (73.3 g) and acetonitrile (330 ml) were stirred at 20° C. to 25° C., under nitrogen. Acetoxyacetyl chloride (28 ml) was added maintaining the temperature at less than 30° C., followed by an acetonitrile line wash (37 ml). The reaction mixture was stirred at ambient for 60 minutes before water (250 ml) and 47% w/w sodium hydroxide solution (77.2 ml) were added followed by a water line wash (25 ml), keeping the temperature at less than 30° C. The reaction mixture was stirred at ambient for 120 minutes before the lower aqueous layer was separated. Water (735 ml) was added to the organic layer and mixture stirred at ambient until a solid crystallised. The solid was filtered, washed with a 50% aqueous acetonitrile (2×90 ml), and then dried in a vacuum oven between 50° C. and 55° C. to give the title product (65.8 g; 83.9% yield); melting point 195.5–196.5° C.; NMR Spectrum: (DMSO $d_6$) 1.64–1.83 (m, 2H); 1.98–2.14 (m 2H); 3.28–3.48 (m, 1H); (m, 2H); 3.57–3.67 (m, 1H); 3.81–3.92 (m, 1H); 4.00 (s 3H); 4.14 (s, 2H); 4.81 (m 1H); 7.27 (s 1H); 7.36 (t 1H); 7.54–7.64 (m 2H); 8.00 (s 1H); 8.66 (s 1H); Mass Spectrum: $(M+H)^{30}$ 460.9.

The 4-(3-Chloro-2-fluoroanilino)-7-methoxy-6-(piperidin-4-yloxy)-quinazoline dihydrochloride ethanol solvate starting material was prepared as follows.

Step 1: Preparation of 4-(3-Chloro-2-fluoroanilino)-6-hydroxy-7-methoxyquinazoline 6-Acetoxy-7-methoxy-4(1H)-quinazolinone (150 g; prepared as described in WO96/15118, Example 39 thereof), N,N-diisopropylethylamine (123 ml) and toluene (1275 ml) were stirred at 70° C., under nitrogen. Phosphorus oxychloride (150 ml) was added over 15 minutes to the slurry at 70° C. The mixture was held at 70° C. for 2 hours to complete the chlorination. A dark brown solution formed after 30 minutes following addition of the phosphorus oxychloride. Toluene (680 ml) was added to the reaction mixture, followed by addition of 3-chloro-2-fluoroaniline (78 ml) over 10 minutes at 70° C. On completion of the addition, a solid precipitated resulting in a beige slurry. The slurry was held at 70° C. for 1 hour and then cooled to ambient temperature. The reaction mixture was filtered and washed with toluene (2×300 ml), aqueous IMS (2×450 ml and IMS (2×450 ml). The solid was left to pull dry on the filter overnight to give 6-acetoxy-4-(3-chloro-2-fluoroanilino)-7-methoxyquinazoline.HCl salt; NMR Spectrum: (DMSO $d_6$) 2.39 (s, 3H); 4.02 (s, 3H); 7.36 (t, 1H); 7.58 (s, 1H); 7.64 (t, 1H); 8.79 (s, 1H) 8.91 (s, 1H); 11.93 (bs 1H); Mass Spectrum: M+H362.

6-Acetoxy-4-(3-chloro-2-fluoroanilino)-7-methoxyquinazoline.HCl salt (about 253 g), methanol (1900 ml) and water (632.5 ml) were stirred at ambient temperature. Sodium hydroxide solution (47% w/w; 108 ml) was added dropwise and the reaction mixture heated to 60° C. to form a dark solution. The solution was held at 60° C. for 1 hour and then screened to a clean vessel. The mixture was cooled to ambient temperature before acetic acid (72.8 ml) was charged. The precipitated solid was filtered, washed with 50% aqueous methanol (500 ml) and methanol (500 ml), and then dried in a vacuum oven at 45° C. to give 4-(3-chloro-2-fluoroanilino)-6-hydroxy-7-methoxyquinazoline; (204.8 g; 75.7% yield); Melting point 265–268° C.; NMR Spectrum: (DMSO $d_6$) 4.01 (s, 3H); 7.24 (s, 2H); 7.32 (t, 1H); 7.51–7.56 (m, 2H); 7.78 (s, 1H); 8.58 (s, 1H); Mass Spectrum: (M+H)$^+$ 320.

Step 2: Preparation of tert-butyl 4-[4-(3-chloro-2-fluoroanilino)-7-methoxyquinazolin-6-yloxy]piperidine-1-carboxylate 4-(3-Chloro-2-fluoroanilino)-6-hydroxy-7-methoxyquinazoline (116.7 g), tert-butyl 4-methylsulfonyloxypiperidine 1-carboxylate (153.1 g), potassium carbonate (75.7 g) and NMP (700 ml), were stirred at 100° C. to 105° C., under nitrogen, for 24 hours. The mixture was cooled to 75° C. to 80° C. before water (1080 ml) was added whilst maintaining the temperature above 70° C. The mixture was stirred at 70° C. to 75° C. for 90 minutes then cooled to 20° C. to 25° C. The resulting solid was filtered, washed with water (2×175 ml), and then dried in the vacuum oven between 50° C. and 55° C. to give tert-butyl 4-[4-(3-chloro-2-fluoroanilino-7-methoxyquinazolin-6-yloxy]piperidine-1-carboxylate; (174.4 g; 95% yield); Melting point: 192–193.5° C.; NMR Spectrum: (DMSO $d_6$) 1.40–1.42 (d, 9H); 1.62–1.72 (m, 2H); 1.99–2.08 (m, 2H); 3.24–3.33 (m, 2H); 3.65–7.73 (m, 2H); 4.00 (s, 3H); 4.76 (m 1H); 7.28 (s; 1H); 7.37 (t, 3H); 7.56 (t, 1H); 7.63 (t, 1H); 8.01 (s, 1H); 8.72 (s 1H); Mass Spectrum: (M+H)$^+$ 503.

Step 3: Preparation of 4-(3-chloro-2-fluoroanilino)-7-methoxy-6-(piperidin-4-yloxy)-quinazoline Dihydrochloride Ethanol Solvate tert-Butyl 4-[4-(3-chloro-2-fluoroanilino)-7-methoxyquinazolin-6-yloxy]piperidine-1-carboxylate (107.9 g), ethanol (1208 ml), concentrated hydrochloric acid (67 ml) and an ethanol line wash (100 ml), were stirred at 70° C. to 75° C. for 2 hours. The mixture was cooled to 60° C. over 1 hour, before a seed of 4-(3-chloro-2-fluoroanilino)-7-methoxy-6-(piperidin-4-yloxy)-quinazoline dihydrochloride$_1$ was added and then cooled to 0° C. to 5° C. over 3 hours. The resulting solid was filtered, washed with ethanol (2×100 ml), and then dried in the vacuum oven between 50° C. and 55° C. to give 4-(3-chloro-2-fluoroanilino)-7-methoxy-6-(piperidin-4-yloxy)-quinazoline dihydrochloride ethanol solvate; (94.3 g; 81.4% yield); Melting point: 212–214° C.; NMR Spectrum: (DMSO $d_6$) 1.89–2.00 (m, 2H); 2.26–2.35 (m, 2H); 3.16–3.35 (m, 4H); 4.02 (s, 3H); 5.09 (s, 1H); 7.36 (t, 1H); 7.42 (s, 1H); 7.52 (t, 1H); 7.64 (t, 1H); 8.83 (s 1H); 8.88–8.97 (m, 2H); 9.09 (bs, 1H); Mass Spectrum: (M+H)$^+$ 403. Note 1: The seed crystals used were obtained using the same synthesis described above, but without the addition of seed crystals and slow cooling.

EXAMPLE 6

2-[4-{4-[3-chloro-2-fluoroanilino]-7-methoxyquinazolin-6-yloxy}piperidin-1-yl]-2-oxoethyl Dihydrogen Phosphate

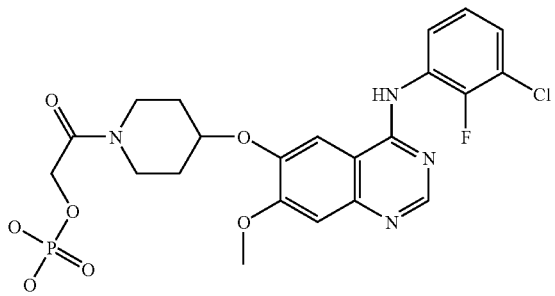

4M Hydrogen chloride in 1,4 dioxane (1.95 ml) was added to a stirred solution of di-tert-butyl 2-[4-(4-[3-chloro-2-fluoroanilino]-7-methoxyquinazolin-6-yloxy)piperidin-1-yl]-2-oxoethyl phosphate (0.951 g) in 1,4-dioxane (16 ml). The mixture was stirred overnight and diethyl ether (50 ml) was then added. The resulting precipitate was collected by filtration and dried to give the title product as a white solid (0.77 g); NMR Spectrum: (DMSO $d_6$) 1.60–1.76 (m, 2H), 2.11 (m, 2H), 3.38 (m, 2H), 3.69 (m, 1H), 3.91 (m, 1H), 4.02 (s, 3H), 4.53 (m, 2H), 5.02 (m, 1H), 7.37 (m, 2H), 7.55 (m, 1H), 7.65 (m, 1H), 8.53 (s, 1H), 8.81 (s, 1H), 11.86 (br s, 1H); Mass Spectrum: (M+H)$^+$ 541.

The di-tert-butyl 2-[4-(4-[3-chloro-2-fluoroanilino]-7-methoxyquinazolin-6-yloxy)piperidin-1-yl]-2-oxoethyl phosphate used as starting material was prepared as follows.

Tetrazole (0.46 g) and di-tert-butyl N,N-diethylphosphoramidite (2.16 g) were added to a stirred solution of 4-(3-chloro-2-fluoroanilino)-6-[1-(hydroxyacetyl)piperidin-4-yloxy]-7-methoxyquinazoline (1.00 g) in DMA (17 ml). The mixture was stirred at room temperature for 1 hour then cooled to 0° C. 30% aqueous hydrogen peroxide (1.23 ml) was added dropwise and the resulting mixture was allowed to warm to room temperature and stir for a further 2 hours. The mixture was then cooled to 0° C. and aqueous sodium metabisulfite was added (10%, 5 ml). After twenty minutes aqueous saturated sodium bicarbonate was added until the solution was basic. The reaction mixture was then extracted with ethyl acetate (3×50 ml) and purified by flash column chromatography on silica to di-tert-butyl 2-[4-(4-[3-chloro-2-fluoroanilino]-7-methoxyquinazolin-6-yloxy)piperidin-1-yl]-2-oxoethyl phosphate as a white solid. (0.951 g); Mass Spectrum: (M+H)$^+$ 653.

EXAMPLE 7

Pharmaceutical Compositions

The following illustrates a representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Injection I | (50 mg/ml) |
|---|---|
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100%. | |

The above formulations may be prepared by conventional procedures well known in the pharmaceutical art. For example the tablet may be prepared by blending the components together and compressing the mixture into a tablet.

The invention claimed is:

1. A quinazoline derivative of the Formula I:

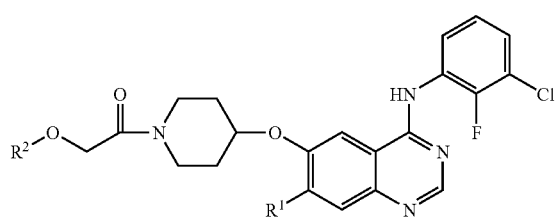

wherein:
R¹ is selected from hydrogen and methoxy; and
R² is hydrogen;
or a pharmaceutically acceptable salt thereof.

2. A quinazoline derivative according to claim 1 which is 4-(3-chloro-2-fluoroanilino)-6-[1-(hydroxyacetyl)piperidin-4-yloxy]-7-methoxyquinazoline;
or a pharmaceutically acceptable salt thereof.

3. A quinazoline derivative according to claim 1 or claim 2 or a pharmaceutically acceptable acid salt thereof.

4. A pharmaceutical composition which comprises a quinazoline derivative of the Formula I, or a pharmaceutically-acceptable salt, thereof, as defined in claim 1 or claim 2 in association with a pharmaceutically-acceptable diluent or carrier.

5. A process for the preparation of a quinazoline derivative of the Formula I, or a pharmaceutically acceptable salt, or a pharmaceutically acceptable salt thereof, which process comprises:

coupling a compound of the Formula II, or a salt thereof:

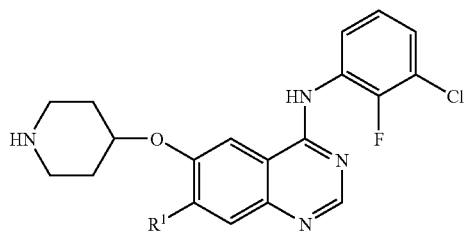

wherein R¹ is as defined in claim 1, and any functional group in the compound of Formula II is protected if necessary;
with a carboxylic acid of Formula III, or a reactive derivative thereof:

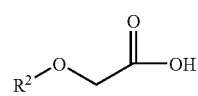

wherein R² is as defined in claim 1, and any functional group in the compound of Formula III is protected if necessary;
and thereafter, if necessary (in any order):
(i) removing any protecting groups by conventional techniques;
(ii) forming a pharmaceutically acceptable salt.

* * * * *